United States Patent [19]
Noble et al.

[11] Patent Number: 5,776,204
[45] Date of Patent: Jul. 7, 1998

[54] ASYMMETRIC HIP STEM

[75] Inventors: Philip C. Noble, Houston, Tex.; Anthony K. Hedley, Paradise Valley, Ariz.; Michael J. Schulzki, Boonton; William J. Kelly, Jr., Clifton, both of N.J.

[73] Assignee: Howmedica Inc., New York, N.Y.

[21] Appl. No.: 653,295

[22] Filed: May 24, 1996

[51] Int. Cl.$^6$ .................................................. A61F 2/32
[52] U.S. Cl. .............................................................. 623/23
[58] Field of Search ............................... 623/18, 19, 23

[56] References Cited

U.S. PATENT DOCUMENTS

| | | |
|---|---|---|
| 3,996,625 | 12/1976 | Noiles . |
| 4,589,883 | 5/1986 | Kenna . |
| 4,714,470 | 12/1987 | Webb, Jr. et al. . |
| 4,718,912 | 1/1988 | Crowninshield . |
| 4,738,681 | 4/1988 | Koeneman et al. . |
| 4,778,475 | 10/1988 | Ranawat et al. . |
| 4,813,963 | 3/1989 | Hori et al. . |
| 4,895,573 | 1/1990 | Koeneman et al. . |
| 5,004,476 | 4/1991 | Cook . |
| 5,139,522 | 8/1992 | Adrey et al. . |
| 5,211,666 | 5/1993 | Fetto . |
| 5,358,534 | 10/1994 | Dudasik et al. . |

FOREIGN PATENT DOCUMENTS

| | | |
|---|---|---|
| 0543099A2 | 5/1993 | European Pat. Off. . |
| 2069340 | 8/1981 | United Kingdom . |
| WO91/18560 | 12/1991 | WIPO . |
| WO94/08534 | 4/1994 | WIPO . |

OTHER PUBLICATIONS

"The S–ROM™ Total Hip System"—Joint Medical Products product brochure; (8 pages); 1989.

"Impact Modular Total Hip System"—Biomet product brochure; (19 pages); 1992.

*Primary Examiner*—David J. Isabella
*Attorney, Agent, or Firm*—Peter C. Richardson; Raymond W. Augustin; Laura G. Barrow

[57] ABSTRACT

An improved asymmetric femoral hip stem component for use in cementless hip replacement procedures is described. The stem comprises a proximal region having a novel three-dimensional configuration to allow for better fit and stability of the stem within the femoral intramedullary canal with minimal removal of strong bone therefrom. The stem further includes a twist isolated in the mid-stem region to improve fit while minimizing enlargement of the femoral canal. A distal end comprising a rotated internal slot is also described, wherein the slot reduces bending stiffness of the stem in both the coronal and sagittal planes.

14 Claims, 12 Drawing Sheets

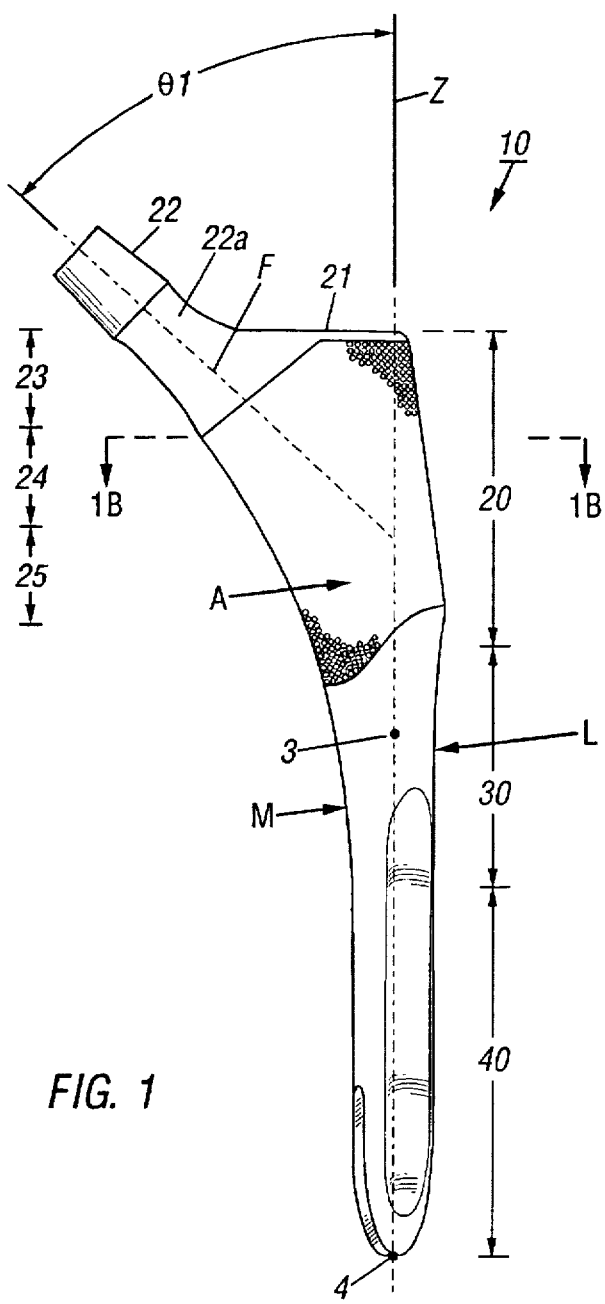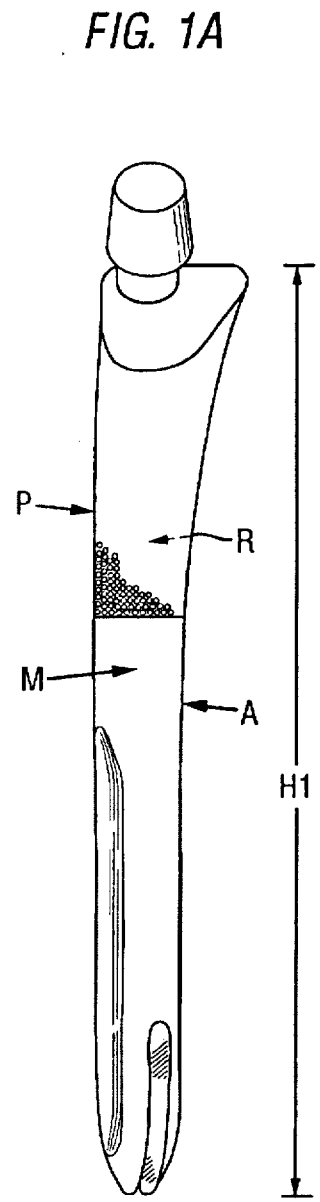

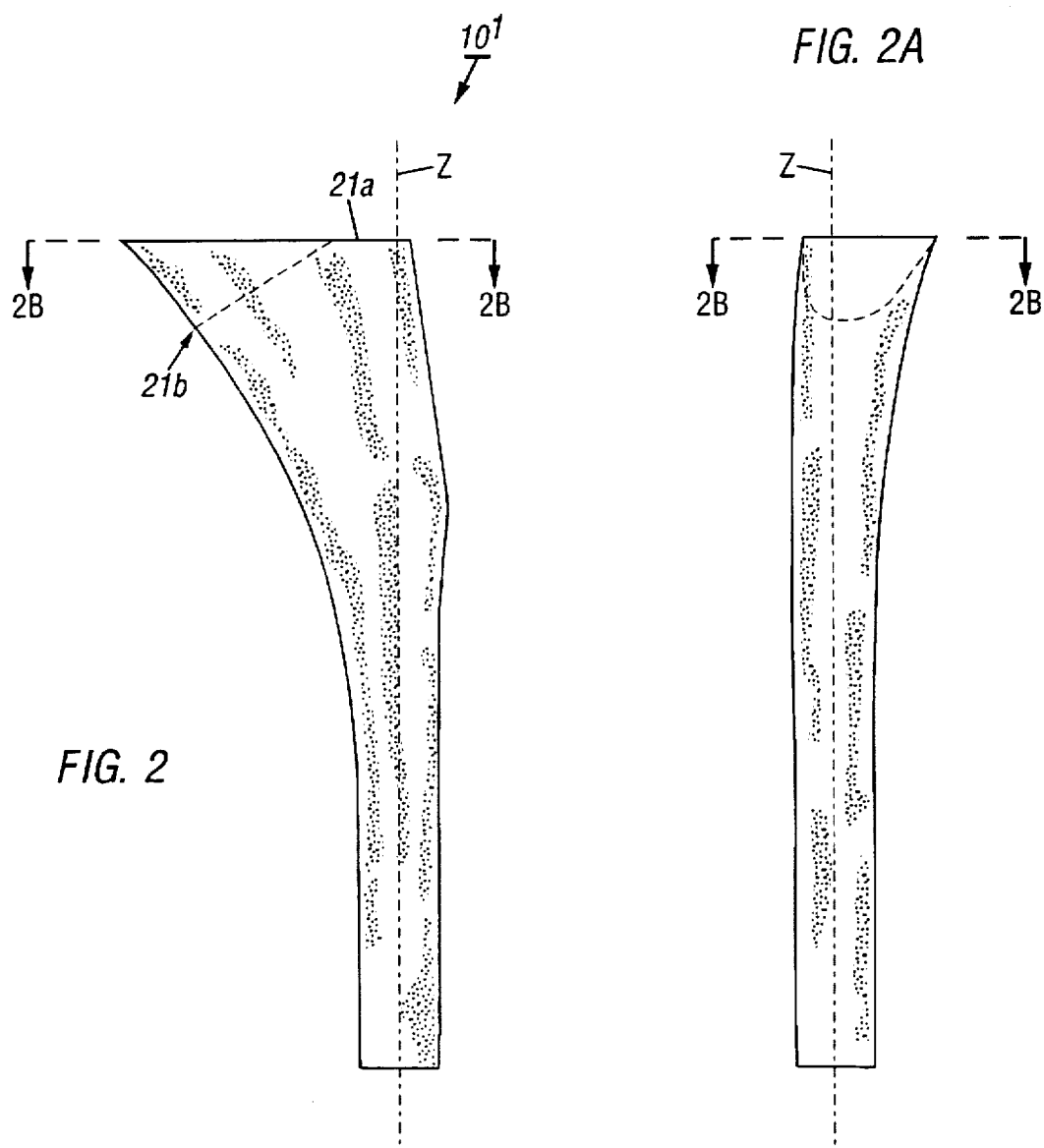

FIG. A-A
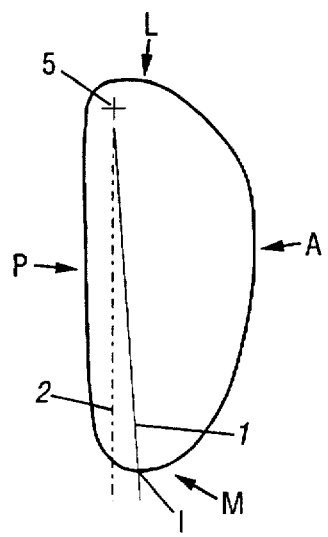
FIG. B-B
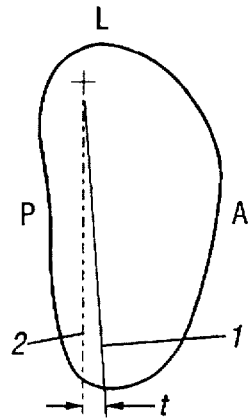
FIG. C-C
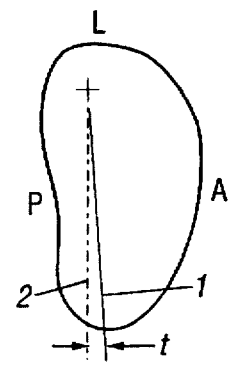
FIG. D-D
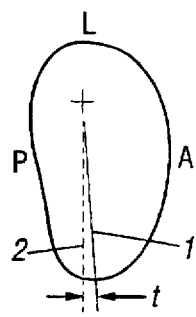
FIG. E-E
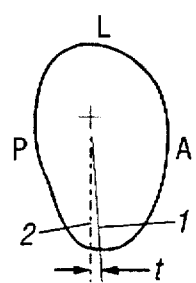
FIG. F-F
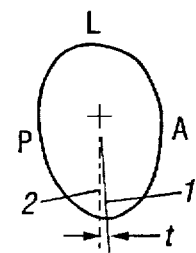
FIG. G-G
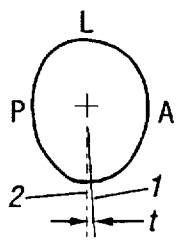
FIG. H-H
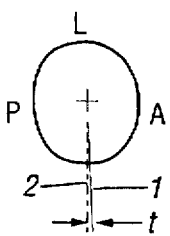
FIG. I-I
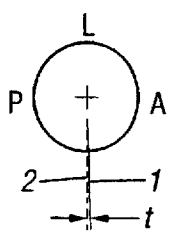
FIG. J-J
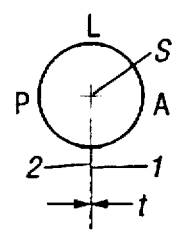

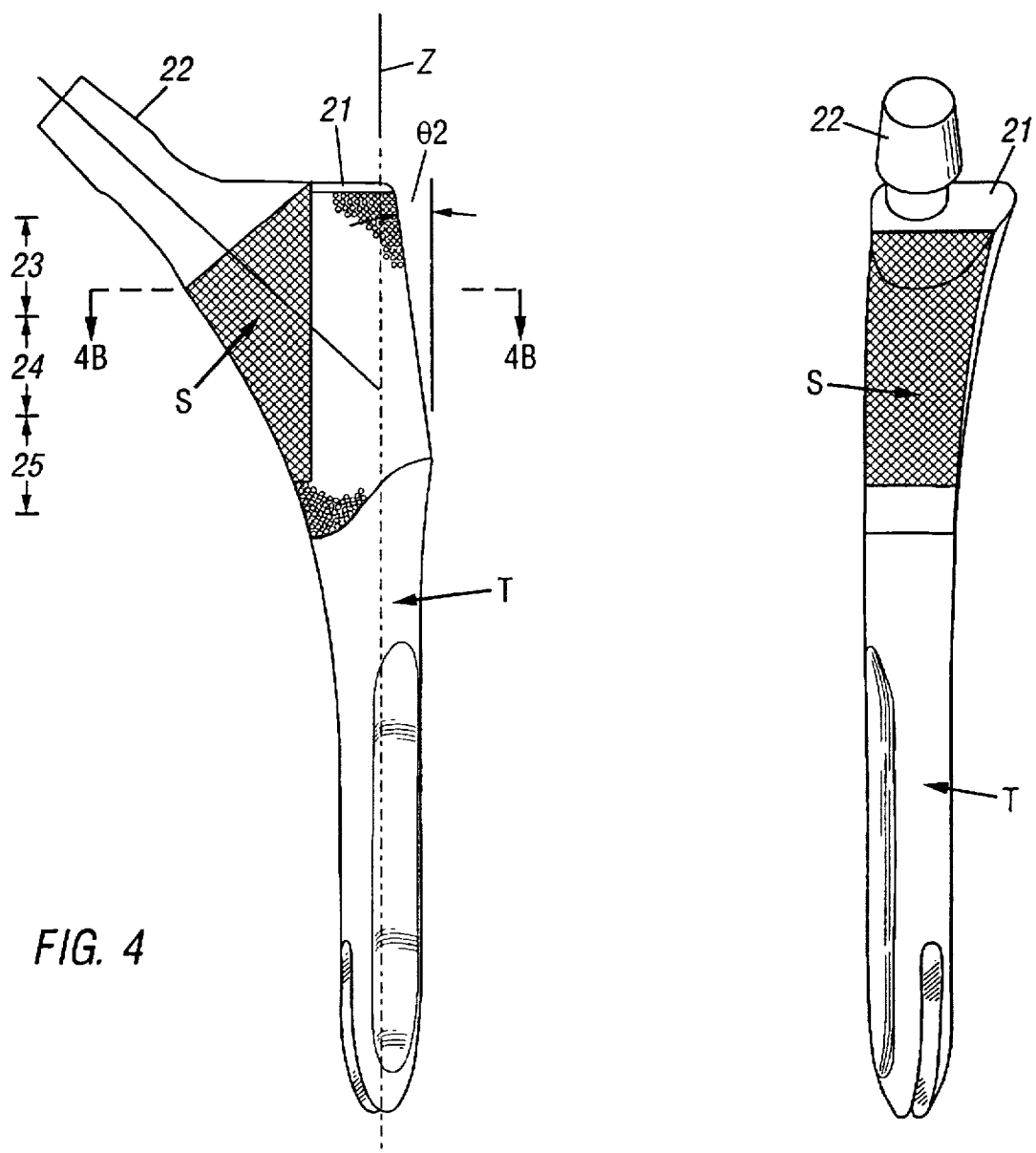

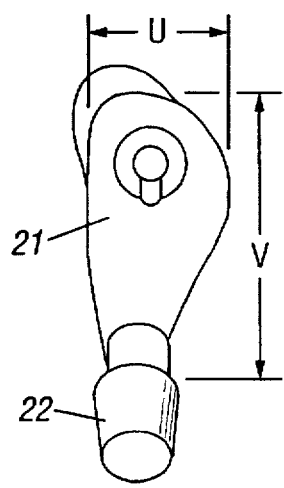
FIG. 7
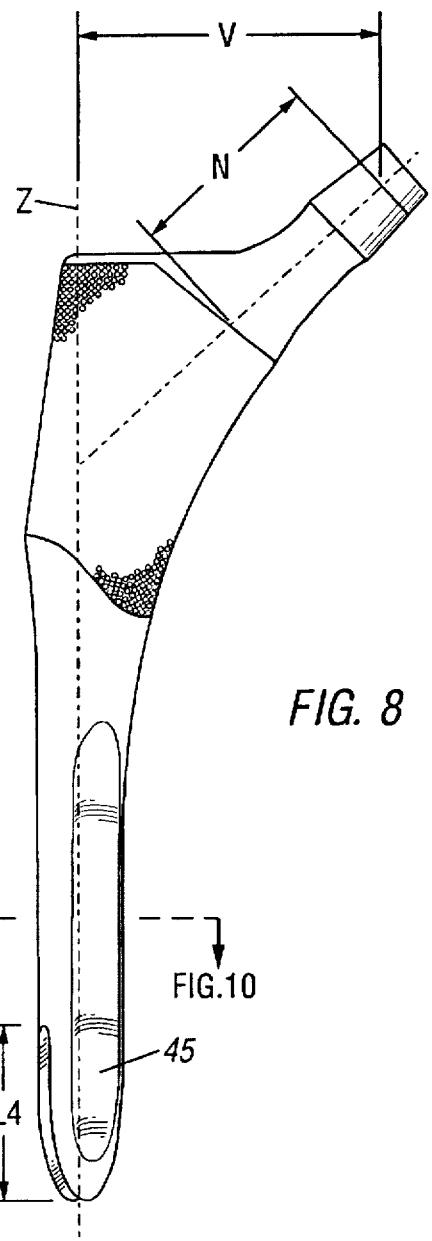
FIG. 8
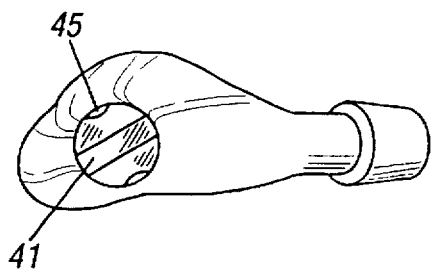
FIG. 9
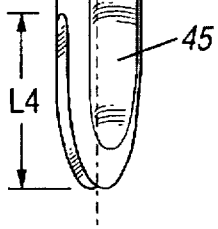

ASYMMETRIC HIP STEM

I. BACKGROUND OF INVENTION

1. Field of Invention

The present invention relates to femoral hip prostheses, and more particularly to a femoral hip stem component having a shape which provides a better fit within the femoral medullary canal.

2. Background of Invention

Hip arthroplasty procedures involve the implantation of a prosthetic stem component within a femoral intramedullary canal. A ball on the proximal end of the stem cooperates with a socket of an acetabulum to provide for articulation between the femur and the acetabulum. In order to maintain pain-free articulation of the hip joint following implantation of the stem, it is important that the stem be securely fastened to the intramedullary canal. Such fastening can be accomplished with a bone cement which adheres to the stem and the wall of the intramedullary canal. In addition numerous stems have been provided with a porous surface as taught in U.S. Pat. Nos. 4,550,448 (Kenna) and 3,605,123 (Hahn) to either accommodate adherence with the bone cement or enhance a press fit between the porous surface and the wall of the intramedullary canal. If a press fit is desired with the intramedullary canal, the stem contour should closely match the contour of the intramedullary canal so that the porous surface is in intimate contact with bone, thereby enabling bone to grow into the porous surface.

Various patents relate to a femoral component for press fit with, and biological fixation to, the wall of the proximal metaphysis and intramedullary canal. U.S. Pat. Nos. 4,589,883 (Kenna) and 4,738,681 (Koeneman et al.) teach a femoral stem having a twist in the proximal region for improved fit and stability within the femoral canal. While this appears to be close to the geometry of the natural femur, in practice the rotational motion of the stem induced by the twist can lead to enlargement of the implantation site and the formation of gaps at the implant/bone interface. The twist in this region also prevents the stem from sitting within the neck of the femur. Instead, the stem sits in the bone in a rotated position, thus making preparation of the implantation site more difficult since surgeons often attempt to change the rotational position of the implant to restore the normal position of the femoral head.

A second limitation existing in the art is the cross-sectional shape of the stem, in particular in the proximal regions of the stem, wherein the geometry often necessitates the removal of strong bone within the femur (e.g. the calcar femorale and the medial border of the greater trochanter) before the stem can be correctly implanted, achieving a close fit to the canal. In practice, this is difficult to achieve with existing surgical instruments, so many such prostheses are difficult to implant without undersizing or misalignment. U.S. Pat. No. 5,358,534 (Dudasek, et al.), as well as Kenna described above, teach a stem wherein a transverse cross-section taken in the proximal region of the stem is substantially rectangular in shape (i.e. it has parallel anterior and posterior edges). Such a shape does not conform well to the internal anatomy of the femoral intramedullary canal and necessitates the removal of the bone from the greater trochanter during implantation. In addition, while the Dudasek stem does disclose the presence of a posterior concavity to clear the posterior cortex of the intramedullary canal, it does not teach or suggest the geometry or dimensions of the concavity for allowing the medullary cavity to be maximally filled with the stem without the need to remove the calcar femorale.

U.S. Pat. No. 4,813,963 (Hori, et al.) is directed to a stem having a configuration that, according to the specification, more accurately reflects the anatomic contour of the intramedullary canal. In particular, the patent teaches a stem wherein the proximal portion, in transverse cross section, has an asymmetric contour to define an anterior side which forms an acute angle with a lateral side, and a posterior side which approaches the anterior side in the medial direction. In addition, the medial side is arcuate in shape while the other sides have linear edges. However, this stem still requires removal of bone from the greater trochanter due to the wide angle of the anterior/lateral edge and the bulk in the posterior/lateral corner. Moreover, although designers of previous prosthetic devices have utilized simple cross-sectional shapes with flat sides to facilitate manufacture of these implants, the inner contours of the femur are arcuate and rarely linear. Consequently, stems such as that taught by Hori, et al. only achieve contact with the femoral cavity at discrete points, typically along relatively sharp edges. This may result in localized stem concentration and could lead to an increased incidence of bone fracture during implantation. In addition, areas of relatively soft bone will be left between the localized points of contact. These areas tend to become osteoporotic with time, leading to less biological attachment of the prosthesis through bony ingrowth. These areas may also act as open channels within the bone structure, making the femur susceptible to infiltrating particles generated by wearing of the artificial joint. The biological reaction to these particles quite frequently leads to erosion of bone around the prosthesis and may cause loosening and failure of the implant.

A third problem with the prior art is thigh pain that is often experienced after cementless total hip arthroplasty. This pain is commonly linked to the stiffness mismatch between the bone and the prosthesis. Provision of a distal slot reduces bending stiffness, thereby reducing subsequent thigh pain. Other beneficial effects of reducing distal bending stiffness include easier stem insertion, lower incidence of distal fractures during stem insertion, and greater ease of implanting the correct size implant. Conventional slotted prostheses, such as those of Thongpreda et al. (EPO 0 543 099A2) and Noiles (U.S. Pat. No. 3,996,625) have slots oriented in the coronal plane, and therefore only provide the foregoing benefits in one plane of bending. In most activities, the force acting on the distal stem is not directed anteriorly or posteriorly, but has a significant medial-lateral component.

II. SUMMARY OF THE INVENTION

In light of the foregoing problems with prior art femoral hip stems designed for cementless hip arthroplasty procedures, it is an object of the present invention to provide stability of the implant/bone interface in resisting forces applied to the femoral head by optimizing the fit between the femoral cortex and the surface of the implant. Specifically, it is an object of the present invention to provide an implant having a surface contoured to match the cortical walls of the femur (a) anteriorly and posteriorly at the level of the femoral neck osteotomy; (b) anteriorly and medially at the level of the lesser trochanter; and (c) anteriorly, posteriorly, and laterally within the femoral mid-stem.

Another object of the present invention is to provide a femoral implant that is contoured to allow for minimal removal of bone during implantation, in particular the bone from the greater trochanter and the calcar femorale.

Another object of the present invention is to provide for maximum ease of insertion of the implant into the femur without undersizing or misalignment.

Still another object of the present invention is to minimize the enlargement of the implantation envelope during insertion of the stem.

Finally, another object of the invention is to minimize bending stiffness of the stem in both the sagittal and coronal planes, thereby reducing the incidence of thigh pain, allowing for easier stem insertion, and reducing the incidence of distal fractures during stem insertion, for example.

These and other objects of the present invention are achieved by providing a femoral component for use in hip arthroplasty procedures that is designed to fit closely the anatomical contours of the femoral intramedullary canal with minimal bone removal. In particular, certain aspects of the present invention are directed to a femoral stem comprising:

(a) a distal region having a distal portion, a center, and a longitudinal axis intersecting the center, the axis further defining the anterior, posterior, medial and lateral faces;

(b) a proximal region including a top end portion; and (c) a mid-stem region positioned between the distal and proximal regions;

wherein the proximal region is configured such that a cross section taken perpendicular to the longitudinal axis includes:

(d) a substantially arcuate anterior side having a varying radius of curvature;

(e) a posterior side having a concavity;

(f) a substantially arcuate medial side; and (g) a substantially arcuate lateral side that slopes anteriorly to define an angle of declination.

The proximal cross section preferably includes a substantially arcuate posterior/lateral corner located such that the distance from the surface of the femoral component to the distal longitudinal axis always exceeds a minimum distance where said distance is larger than or equal to the diameter of the drive shaft of a rigid drill or reaming instrument which may be used to machine the medullary canal.

Certain aspects of the present invention further include two adjacent geometric bodies, a femoral neck segment and a medullary segment, which as best illustrated in transverse cross sections of the proximal region, are oriented at an acute angle with respect to one another.

The present invention is also directed to a femoral stem having a posterior concavity positioned in the proximal region of the stem, wherein the concavity is configured to preserve the calcar femorale present in the region of the lesser trochanter. Other features of the inventive stem include a cant or taper on the lateral face of the proximal region of the stem in the medial direction which, in combination with the transverse cross section geometry of the proximal region, allows for minimal bone removal from the greater trochanter.

Other aspects of the present invention include the presence of a stem twist about the longitudinal axis, most preferably restricted to the mid-stem region, such that a constant twist angle exists in the proximal region of the stem. Isolation of the stem twist in this region as opposed to the proximal region minimizes enlargement of the implantation envelope caused by such twisting while at the same time provides improved implant fit and stability upon implantation.

The present invention is also directed to a femoral stem having an internal distal slot that is rotated to the coronal plane, preferably about 30 degrees, to reduce the bending stiffness of the stem in both the sagittal and coronal planes.

The foregoing objects and features of the invention, as well as other objects and features, will become more fully apparent when the following detailed description of the invention is read in conjunction with the accompanying drawings.

III. BRIEF DESCRIPTION OF THE DRAWINGS

FIGS. 1 and 1A are an anterior and medial views, respectively, of a left femoral stem.

FIGS. 2 and 2A are anterior and medial views, respectively, of a solid model for which the three-dimensional shape of the femoral stem is derived.

Figure 3:
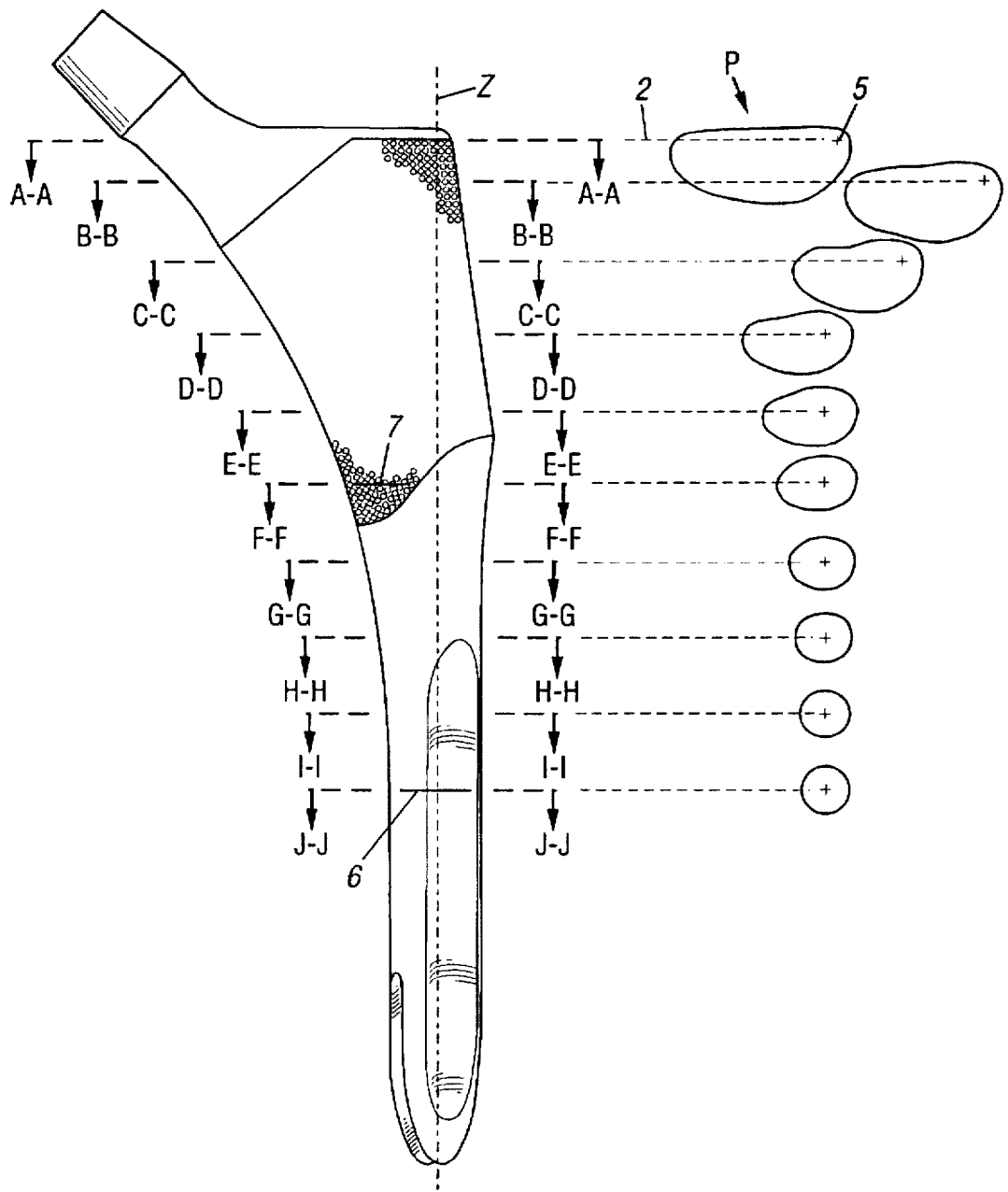
FIG. 3 is an anterior view of a left femoral stem illustrating several transverse cross-sections A—A through J—J.

FIGS. A—A through FIGS. J—J are enlarged views of the respective cross-sections taken in FIG. 3.

FIGS. 4 and 4A are anterior and medial views, respectively, of a left femoral stem illustrating the medullary and femoral neck segments of the stem.

Figure 4B:
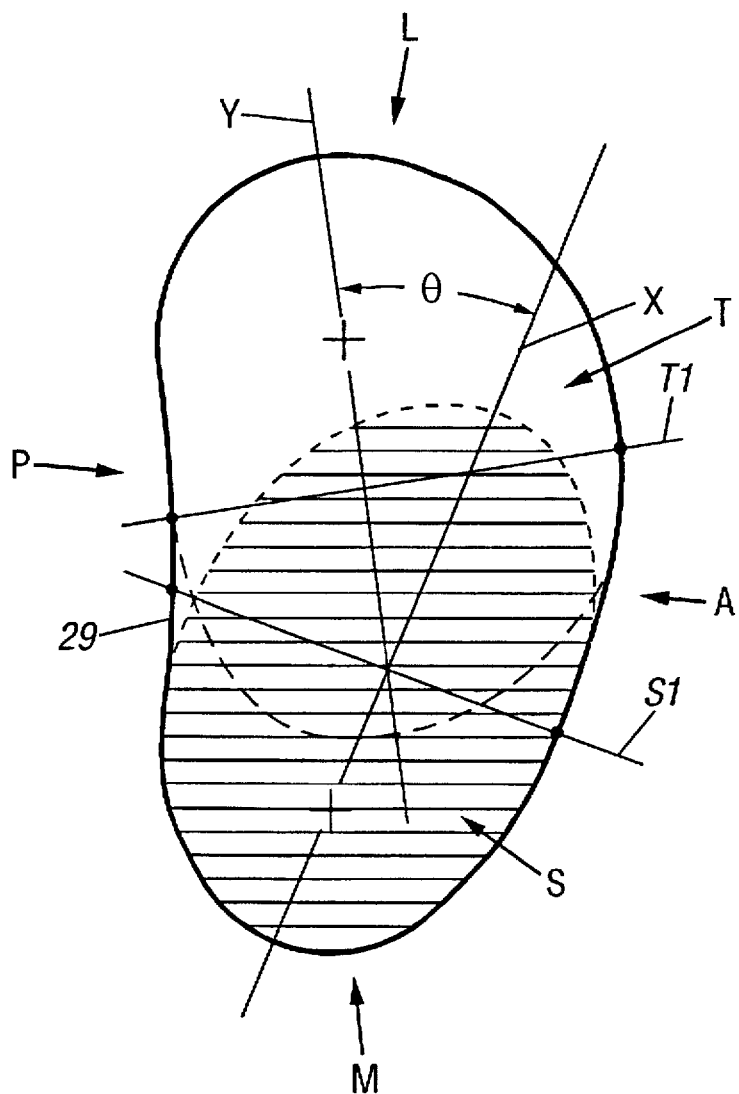

FIG. 4B is a transverse cross-section taken along line 4B—4B in FIG. 4.

Figure 5:
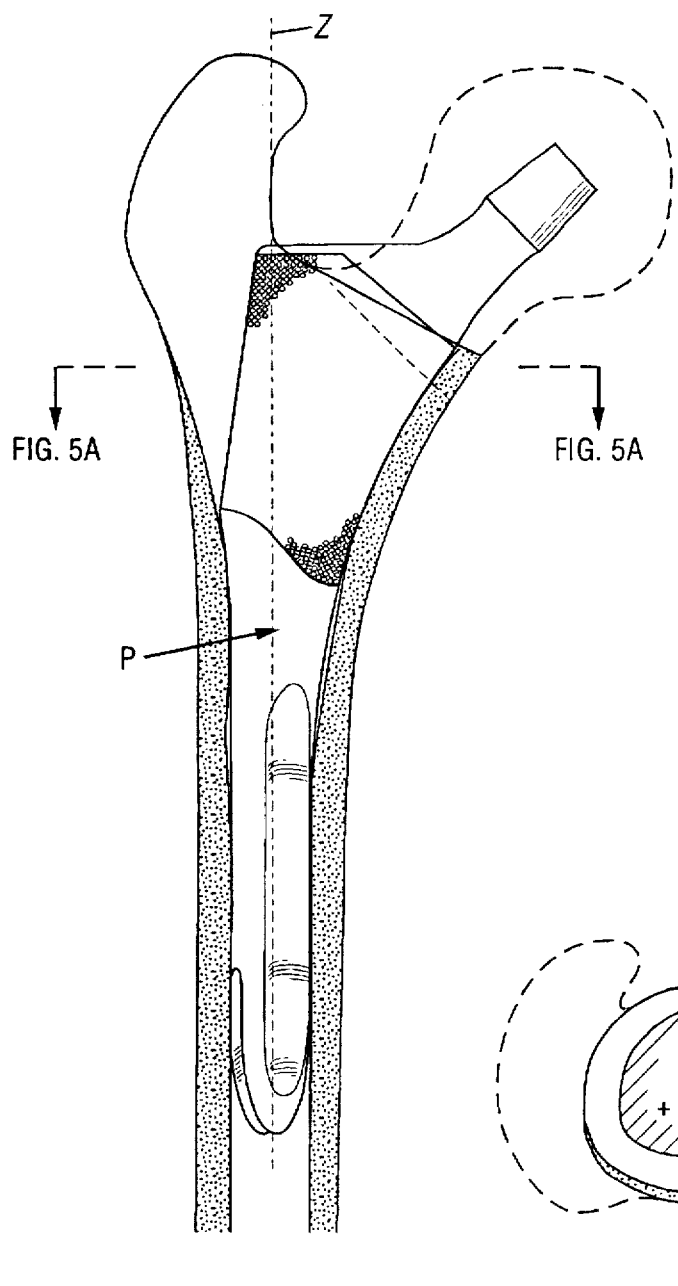

FIG. 5 is a posterior view of a left femoral stem seated within the femur.

Figure 5A:
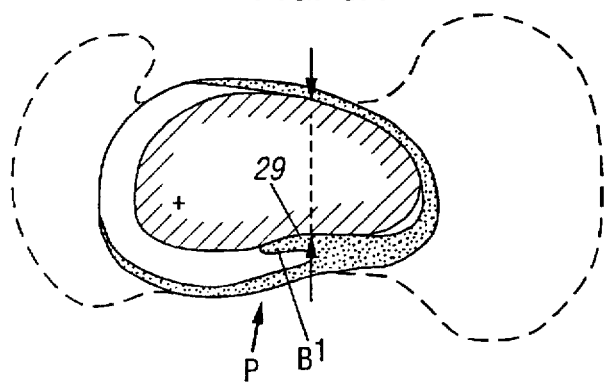

FIG. 5A is a transverse cross-section view of the stem/femur taken along lines 5A—5A in FIG. 5.

Figure 6:
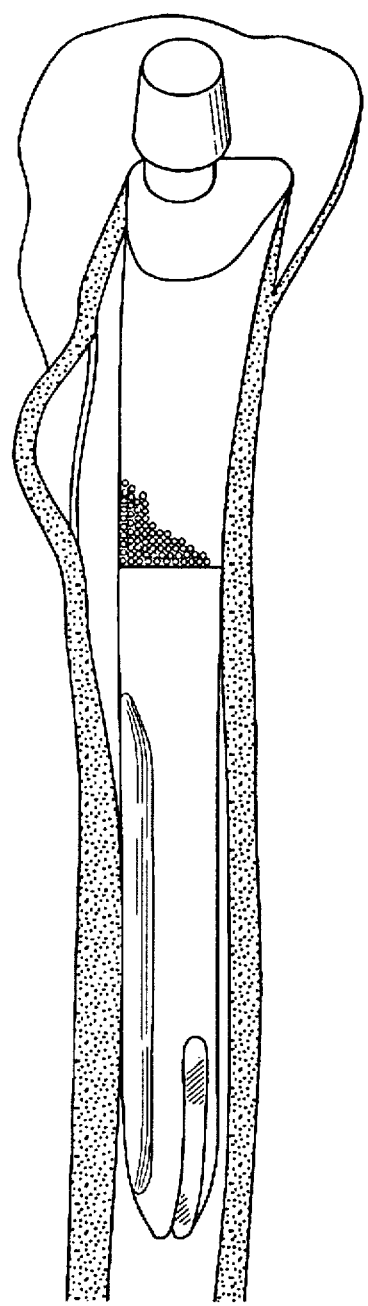

FIG. 6 is a medial view of a left femoral stem seated within a femur.

FIG. 7 is a top plan view of the femoral stem.

FIG. 8 is another anterior view of the left femoral stem.

FIG. 9 is a bottom plan view of the femoral stem.

Figure 10:
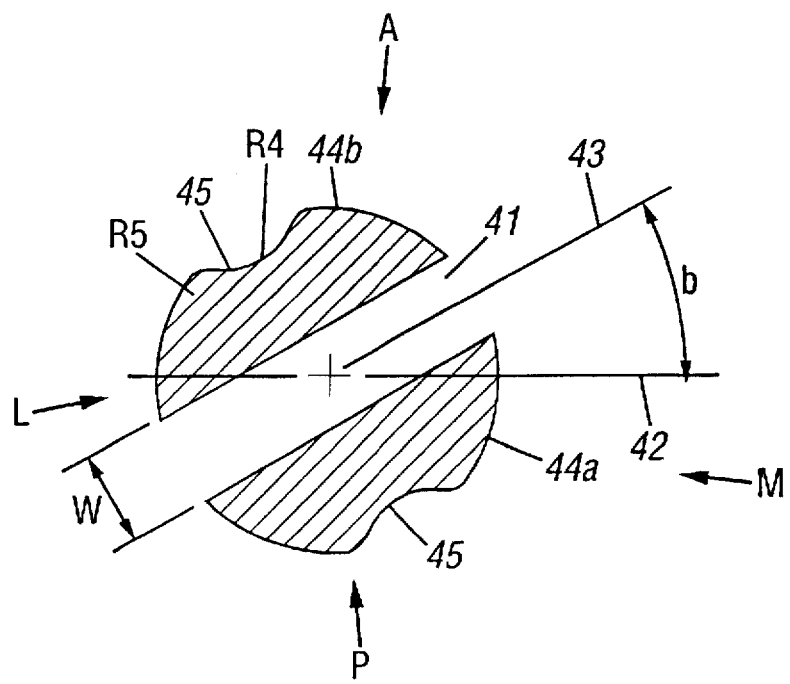

FIG. 10 is a transverse cross section view of the distal region of the stem taken along lines 10—10 of FIG. 9.

Figure 11:
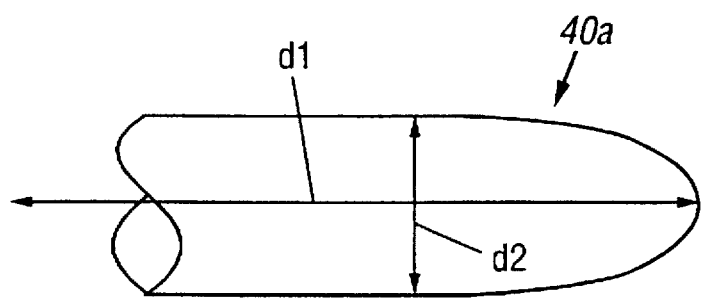

FIG. 11 is a schematic side view of the stem illustrating the elliptical configuration of the distal end.

IV. DETAILED DESCRIPTION OF THE PREFERRED EMBODIMENTS

The present invention is directed to am improved asymmetric femoral stem for implantation into a proximal femur. More particularly, certain aspects of the invention are directed to a femoral stem that comprises several key features that provide an optimum balance of the following factors:

(a) stability of the implant/bone interface in resisting forces applied to the femoral head;

(b) minimum removal of bone during implantation;

(c) maximum ease of insertion of the prosthesis into the femur without undersizing or misalignment; and (d) minimum enlargement of the "implantation envelope" during insertion of the stem.

Figure 1B:
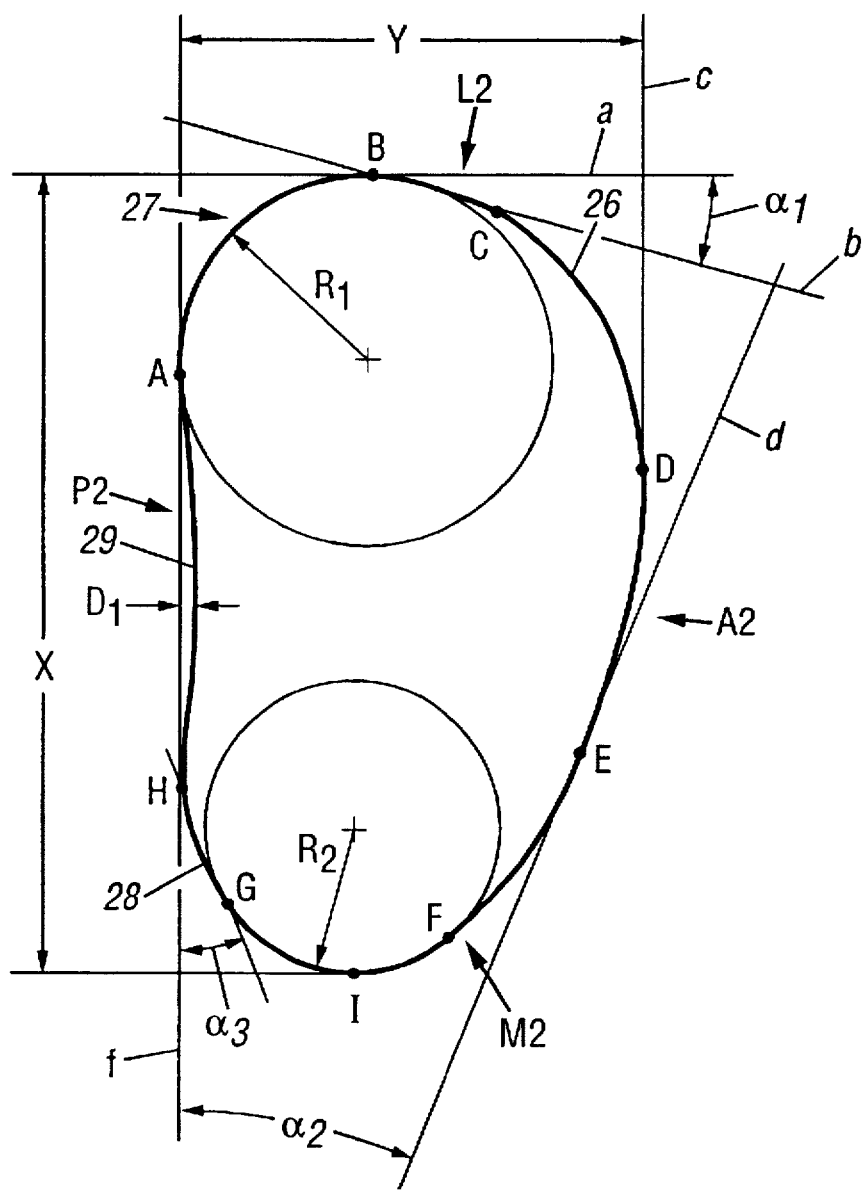
FIG. 1B is a transverse cross-section of the stem taken along lines 1B—1B in FIG. 1.
Figure 1B:
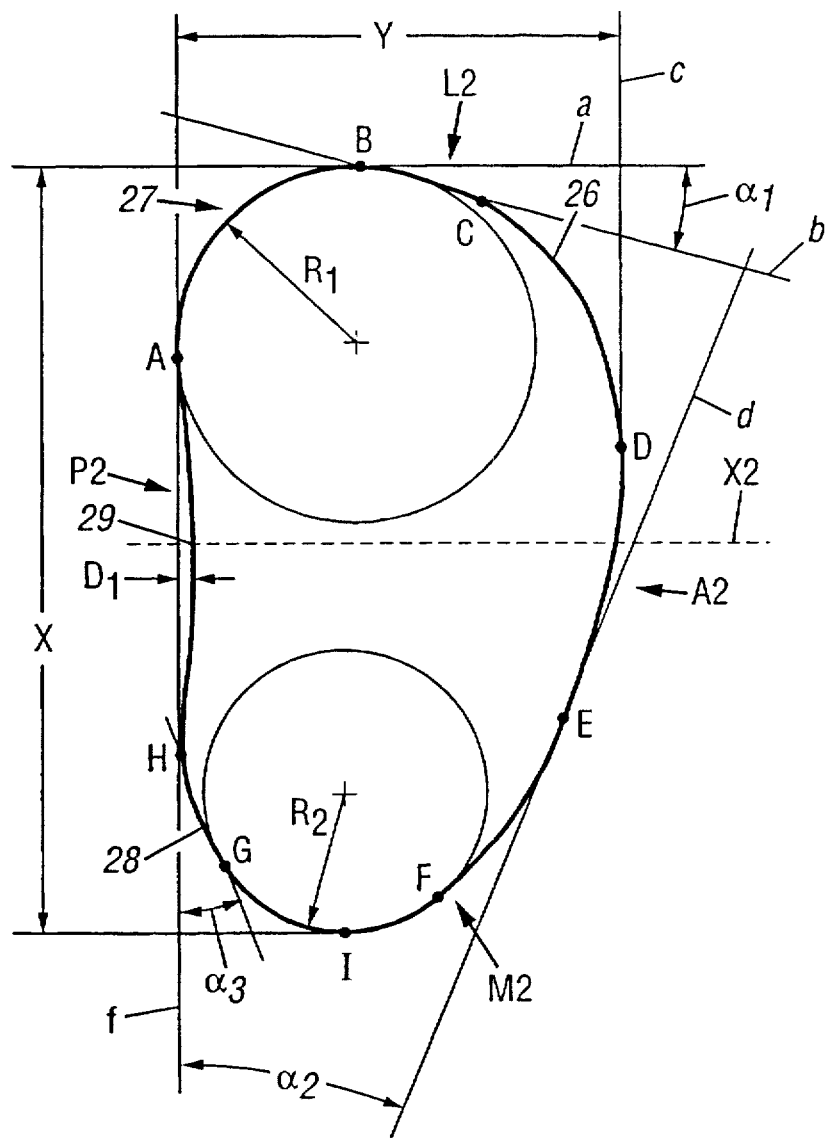

Referring now to the figures, a left femoral stem component (10) is illustrated and comprises a proximal region (20), a distal region (40), and a mid-stem region (30) positioned therebetween, with each region most preferably comprising about one-third of the total length of the stem (FIG. 1). The total length (H1) of the stem (10) preferably ranges from about 4.5 inches to about 6.5 inches (FIG. 1A). The stem further includes a longitudinal or distal axis (Z) which corresponds with the distal center (5) in the distal region (40) (See FIGS. 3 and FIGS. A—A through J—J). Unlike some conventional stems, the posterior face (P) of the proximal region, as shown in FIG. 1A, has only a slight bow generally extending in the proximal-distal direction, with a relatively large radius (R) measured from the anterior face (A), as shown in FIG. 1A, thereby minimizing the potential for enlargement of the femoral cavity upon implantation. Moreover, the overall design of the implant, which is discussed in greater detail below, allows for a higher femoral neck osteotomy, most preferably about 5 mm higher than for conventional hip replacement procedures (i.e. about 18 mm above the lesser trochanter).

The inventive stem may be fabricated from conventional materials, most preferably cobalt-chromium-molybdenum alloy (VITALLIUM by Howmedica, Inc.). In a preferred embodiment, the final finish of the implant is satin except in the tapered trunion (22) and between points 3 and 4, as shown in FIG. 1 (i.e. comprising the entire distal region and portion of the mid-stem region), both areas of which have a bright polish finish (FIG. 1).

For ease of explanation, the remaining disclosure is divided into three sections. Section I is directed to the proximal region of the inventive stem, Section II is directed to the mid-stem region, and Section III is directed to the distal region of the stem. It should further be noted that while the description of the invention and the related figures are directed to the left femoral component, the present invention is also applicable to a right femoral component, which is merely a mirror image of the left component described and illustrated herein.

I. Proximal Region

Referring now to FIGS. 1 and 1A, the proximal region (20) comprises approximately the upper one-third of the stem and is preferably covered with a porous coating (discussed in more detail below). The preferred length of the proximal region ranges from about 1.5 inches (for a stem having a total length of about 4.5 inches) to about 2.5 inches (for a stem having a total length of about 6.5 inches). The proximal region is further divided into a proximal section (23) including a top end portion (21) and neck (22a), a central section (24), and a distal section (25).

Figure 2B:
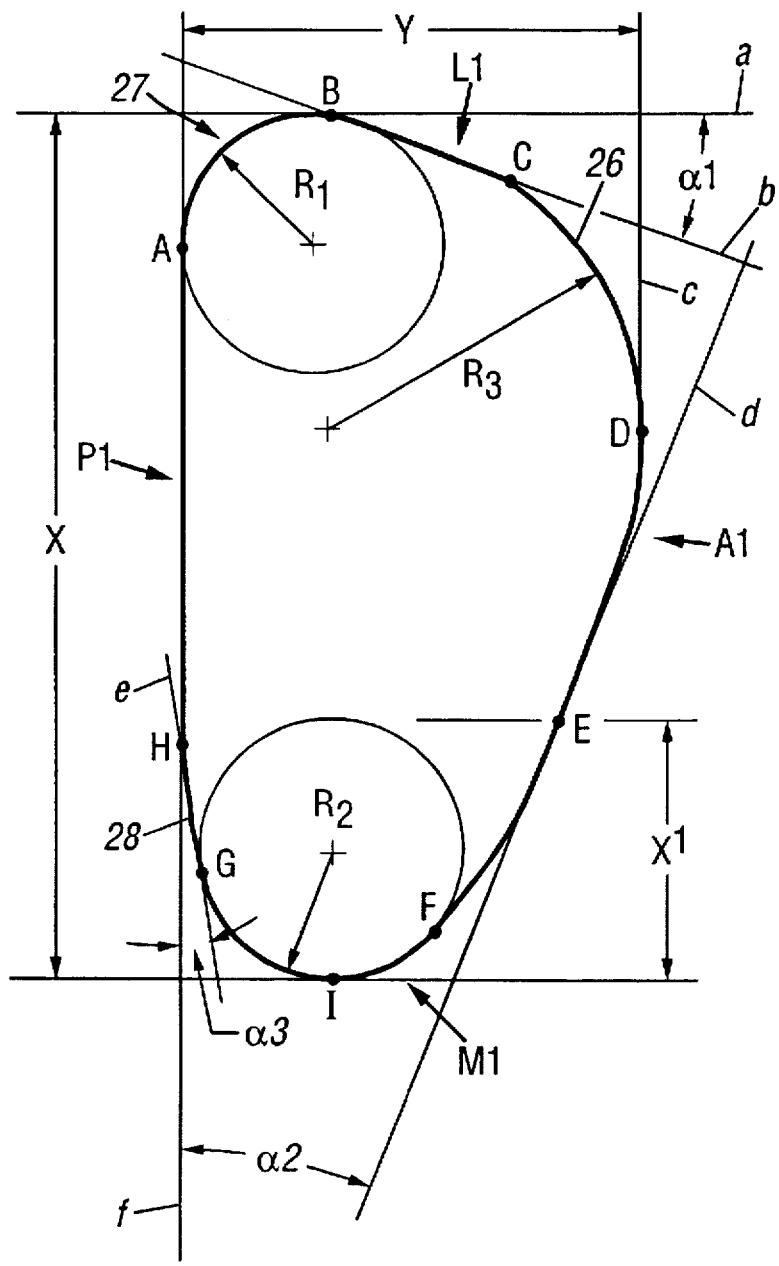
FIG. 2B is a transverse cross-section of the solid model taken along lines 2B—2B in FIG. 2.

The inventive stem was derived from a solid model ($10^1$), as illustrated in FIGS. 2, 2A, and 2B, which was developed to represent the three-dimensional shape of the object that would provide optimum fit to the femoral cavity.

The solid model ($10^1$) has a flat top surface (21a) that is located at the same level along its longitudinal axis (Z) as the top surface (21) of the prosthesis. The shape of the inventive stem (10) matches the shape of the solid model ($10^1$) below the level of the femoral neck osteotomy. The shape of the stem is derived from the solid model by removing all material above the sloped upper surface (21b) corresponding to the femoral neck osteotomy. The prosthetic neck (22a) (FIG. 1) is then added to the sloped surface (21b) and its surface contours are blended into those of the sectioned solid model. Additional surface features may be added to the solid model to modify the bending stiffness of the distal stem or to accommodate the presence of the porous coating, as discussed further below.

The transverse cross-sectional shape of the solid model ($10^1$) and stem (10) varies continuously from proximal to distal, as shown in FIGS. A—A through J—J, which illustrates typical cross-sections through the inventive implant. This shape was derived to contact several key areas that are critically positioned in three-dimensional space to maximize contact between the implant and the femoral cortex, in particular in the region of the greater trochanter where the removal of bone may be minimized.

Specifically, the shape of the solid model may be defined in three-dimensional space by a series of profiles defined by anterior, posterior, lateral, and transverse projections of the surface of the implant. The transverse shape of the solid model, as shown in FIG. 2B, for example, was developed from iterative trials using prototypes that were implanted into cadaveric femora and sectioned transversely. Specifically, FIG. 2B illustrates the top-end view section of the solid model, wherein dimension (X) represents the lateral/medial width of the section and dimension (Y) represents the anterior/posterior width of the section. The proximal cross section comprises a substantially arcuate lateral side (L1) that slopes in the anterior direction to form an angle of declination ($\alpha_1$). This "sloping" geometry of the lateral side allows a stem of maximum medial/lateral width (X) to be implanted into the femur without the necessity of resectioning the medial wall of the greater trochanter for easier insertion of the stem within the bone for an improved fit therein. Most preferably, the sloping of the lateral side (L1) may be defined by a line (a) having tangential contact with the lateral side at its lateral-most point (B), wherein the line (a) is positioned parallel to the sagittal plane. The lateral side (L1) slopes anteriorly to have tangential contact with a second line (b) at a second point (C), such that line (a) intersects line (b) to form an acute angle of declination ($\alpha_1$) therebetween. Preferably, this angle is from about 10 degrees to about 35 degrees in the lateral-medial direction, most preferably about 20 degrees.

The cross-section in FIG. 2B further includes a substantially arcuate anterior side (A1) having a varying radius of curvature displaced laterally. Preferably, the anterior side is configured such that it has tangential contact with a line (c) at point (D) such that line (c) is parallel to the coronal plane and is thus perpendicular to line (a). The anterior side slopes medially to form tangential contact with a line (d) through point (E) and perpendicular to line (b), such that line (d) is oriented at an acute angle ($\alpha_2$) with respect to line (c). Preferably, the angle ($\alpha_2$) is from about 10 degrees to about 30 degrees, most preferably about 20 degrees. Typically, point (E) is located a distance ($X^1$) lateral to the medial-most point of the cross-section (I), wherein $X^1$ is equal to 0.30X (i.e. 30% of the medial/lateral width).

The cross-section in FIG. 2B also includes a substantially arcuate medial side (M1), preferably defined between points G and F, and having a radius (R2) as well as a medial-most point I. Also present is a substantially non-convex, preferably planar, posterior side (P1), and a substantially arcuate posterior/lateral corner (27) defined between points A and B and having radius (R1). Alternatively, the posterior side may be concaved. Further, in the preferred embodiment, the center of the circle defining the posterior/lateral corner (27) is located at the point of intersection between the top surface of the solid model (21a) and the distal longitudinal axis. The radius of the corner (R1) is large enough to allow a rigid reamer to be placed in the intramedullary canal such that the longitudinal axis of the reamer and the canal coincide without a gap subsequently being formed in the vicinity of the posterior/lateral corner. This necessitates that the radius (R1) be larger than, or equal to, the diameter of the drive shaft of the rigid reamer.

The key level for fit and stabilization of the stem within the femur extends from the level of the femoral neck osteotomy to the base of the lesser trochanter. The transverse cross-sectional shape of the stem in this region of the bone may be described by a series of lines and arcs as shown in FIG. 1B. Cross-sections taken at this level along the longitudinal axis are similar in configuration to the more proximal cross-sections of the solid model illustrated in FIG. 2B and include a substantially arcuate anterior side (A2), substantially arcuate medial side (M1) defined between point G and F, and a lateral side (L1) that slopes anteriorly to define an angle of declination ($\alpha_1$) as described above in FIG. 2B. The posterior/lateral corner (27) is defined by points A and B and has a radius (R1) that is somewhat larger than that present at the more proximal levels (as illustrated in FIG. 2B), and preferably is larger than the radius (R2) of the medial side (M2).

Another particularly useful aspect of the stem in this region is the inclusion of a small posterior-medial transition region (28) extending from the posterior side (P2) at point (H) to the medial radius at point (G). As illustrated, this transition region (28) has a radius larger than that defined by the medial side (M2). The transition region may further be approximated by a line (e) intersecting points H and G and inclined at an angle ($\alpha_3$) ranging from about 5 degrees to about 15 degrees in the medial/lateral direction (i.e. relative to line f), most preferably about 8 degrees. This latter feature is particularly preferred since it allows the stem to fit the profile of the femur both within the base of the femoral neck and within the medial arc. Conversely, use of a single arc to connect points H and F leads to a stem profile that contacts the cortical wall of the femur at one point within the posterior-medial corner. This leads, potentially, to an area of localized stress concentration and increased risk of femoral fracture.

The proximal cross section of the stem further includes an overall configuration that can be defined by an axis (X2) bisecting the cross-section through the anterior and posterior sides, wherein the axis (X2) is an equidistance from the lateral-most point (B) and from the medial-most point (I), as illustrated in FIG. 1B. The resulting two sections defined by axis (X2) have different total areas, with the section including the lateral side (L) of the stem having a larger area than that of the adjacent section containing the medial side (M).

The foregoing geometry illustrated in both FIGS. 1B and 2B, in particular the shape of the lateral, medial, and anterior sides, and the posterior/lateral and posterior/medial corners, for example, allows the stem to avoid strong bone in the greater trochanteric region, thereby minimizing bone removal in this area of the intramedullary canal for improved stability. Moreover, the posterior side (P2) includes a concavity (29), as illustrated in FIG. 1B, for example. The concavity generally begins below sectional line A—A, to and including, cross-sections E—E (as illustrated in the corresponding figures), and is designed to allow retention of the strong bone of the calcar femorale at the level of the lesser trochanter, thereby increasing the ease of insertion of the implant as well as the resistance of the femur to rotational deformation. This further facilities implantation of the largest possible prosthesis that the medullary cavity can accommodate, thus preventing undersizing which is the most common cause of implant failure. The preferred depth (D1) of the concavity increases from the proximal-most section to the central section of the proximal region, and then decreases again. This depth (D1) ranges from about 0.1 mm (in the proximal (23) and distal sections (25)) to about 3.0 mm (in the central section (24)).

The foregoing transverse configurations also illustrate another preferred aspect of the inventive stem, specifically two intersecting segments corresponding to two adjacent geometric bodies: a femoral neck segment (S) and a medullary segment (T) (FIGS. 4 and 4A). In the transverse plane, as shown in FIG. 4B, the medullary segment (T) is positioned at an angle ($\theta$) relative to the femoral neck segment, as discussed in more detail below. Such positioning allows the implant to contact the following areas simultaneously: anteriorly and posteriorly at the level of the femoral neck osteotomy; anteriorly and medially at the level of the lesser trochanter; and anteriorly, posteriorly, and laterally within the femoral mid-stem.

Specifically, the femoral neck segment (S) comprises a triangular portion (21) of the proximal region and extends from the top end portion to the distal section (25) of the proximal region along, and including, the medial face (M) of the stem. This is best illustrated in FIGS. 4 and 4A, wherein the lined region indicates the femoral neck segment (S), and the remaining portion of the stem comprises the medullary segment (T). The femoral neck segment (S) is further configured such that a transverse cross section taken perpendicular to the distal or longitudinal axis (Z) comprises a section (lined region) corresponding to the femoral neck segment (S) that is preferably elongated, most preferably generally elliptical, and includes a minor axis (S1) passing through the section and intersecting the anterior (A) and posterior (P) sides. The section further includes a major axis (X) perpendicular to the minor axis (S1) that passes through the medial (M) and lateral (L) sides.

The medullary segment (T) is the remaining portion of the proximal region positioned adjacent to the femoral neck segment and extends from, and includes, a part of the top end portion (21) and lateral face (L), and the distal (40) and mid-stem (30) regions of the stem, as illustrated in FIGS. 4 and 4A (unlined region). The medullary segment (T) is further configured such that a transverse cross section taken perpendicular to the distal or longitudinal axis (Z) also comprises a section similar to that of the femoral neck segment, including a minor axis (T1) passing through the medullary segment and intersecting the anterior (A) side, and a major axis (Y) perpendicular to the minor axis (T1) and intersecting the lateral side (L). The two segments are further oriented with respect to each other such that the two major axes form an acute angle ($\theta$) therebetween. Preferably, the angle ($\theta$) ranges from about 15 to about 50 degrees, most preferably about 32 degrees. As discussed, the inventive stem preferably has a posterior concavity (29), which in this embodiment, as illustrated in FIG. 4B, is positioned at the junction between these two segments.

The proximal region most preferably includes a lateral face that is steeply tapered in the medial direction, thus allowing the posterior/lateral corner (27) of the stem to lie closer to the longitudinal axis (Z) of the stem, as illustrated, for example, in FIGS. 3 and A—A through D—D, thereby resulting in minimal bulk in this region. Consequently, such lateral and posterior/lateral geometry allows for minimal bone removal from the greater trochanter during implantation as well as minimizing the enlargement of the implantation envelope during insertion of the stem. Preferably, the lateral face is tapered at angle ($\theta_2$) ranging from about 5 degrees to about 14 degrees, most preferably about 8 degrees, as shown in FIG. 4, for example.

FIGS. 5 and 6 illustrate a left femoral component of the present invention seated within the intramedullary canal of the femur. FIG. 5A further illustrates the ability of the posterior concavity (29) to fit around the calcar femorale ($B^1$), thereby minimizing its removal.

Referring now to FIGS. 1, 7 and 8, the top-portion (21) of the stem further includes neck (22a) which, in the preferred embodiment, receives a modular femoral head component (not shown). The neck is inclined at an angle of approximately 2 degrees of anteversion in the sagittal plane (i.e. the anterior/posterior direction). In the coronal plan, the neck is positioned at an angle ($\theta_1$) relative to the longitudinal axis (Z) ranging from about 45 degrees to about 55 degrees, more preferably about 48 degrees, as shown in FIG. 1.

As shown in FIGS. 7 and 8, the shape of the proximal region is such that the dimension (V) of the coronal plane (from medial face to lateral face) is larger than the dimension (U) in the sagittal plane (from anterior face to posterior face). Such relative dimensions increase the range of motion of the femoral head approximately 10 degrees per side which totals 20 degrees in the anterior and posterior direction. [Dimension (V) preferably ranges from about 1 inches to about 2 inches. Dimension (U) preferably ranges from about 0.5 inches to about 1 inch.] A preferred femoral head for use with the present invention is a V-40 head manufactured by Howmedica, Inc., which has a 5°-40' taper ranging from −4 mm offset to +16 mm offset in multiple head diameters. The foregoing anterior/posterior and medial/lateral dimensions (U,V) allow for the use of the V-40 heads as well as similarly designed heads without necessitating a skirt.

Preferably the proximal region includes a circumferential porous coating as indicated by the shaded portions in FIGS. 1, 3, 5, 6, and 8, for example. This composition and method of application to the femoral stem is taught, for example, in U.S. Pat. No. 4,550,448 (Kenna), which is incorporated herein by reference. The porous coating is designed to promote bony ingrowth, which in turn creates a bio-seal to prevent the migration of particulate debris.

II. Mid-stem Region

It is recognized in the art that providing a twist in the stem allows the stem to conform to the shape of the femoral cavity more readily during implantation. Certain conventional femoral stems comprise a twist that occurs in the proximal region or substantially throughout the entire length of the stem. A disadvantage in having a twist in the proximal region of the prosthesis is that, upon implantation, the axial rotation of the stem that occurs due to the twist contributes to the enlargement of the anterior and posterior walls of the femoral cavity and subsequent formation of gaps between the stem and the bone. In the present invention, this problem is alleviated by restricting the twist to the mid-stem region of the stem where a tight cortical fit is not generally present. This allows the stem to be seated in the femoral canal with minimal rotation during terminal stages of seating.

As illustrated in FIGS. 1 and 3, for example, the mid-stem region (30) of the hip stem is generally the region between cross-sectional lines F—F to J—J. Preferably, the length of the mid-stem ranges from about 2 inches (for a smaller stem) to about 2.5 inches (for a larger stem). In the present invention, the stem has a twist extending throughout the mid-stem region, beginning generally at the distal boundary (6) of the mid-stem region (i.e. at cross-section line J—J), extending in the proximal direction, and ending at the proximal boundary (7) of the mid-stem region (i.e. at cross-section line F—F) to provide a constant twist angle (t) at the proximal boundary relative to the distal boundary which is consistent throughout the proximal region of the stem.

The twisting of the stem is best illustrated in FIG. 3 and FIGS. A—A through J—J. As shown, cross-sections A—A through J—J are taken perpendicular to the longitudinal axis (Z) of the stem. Line (1) is drawn from the distal center (5) to the medial-most point of each cross-section. In proceeding from the distal end beginning at section J—J to the proximal region, the stem twists about the longitudinal axis (Z) of the stem such that the medial-most point shifts anteriorly. Broken line (2) represents the original line from the distal center (5) to the medial most point of the distal region (40). Thus, for cross-sections distal to section J—J, line (1) and line (2) are identical. The twisting of the stem continues in the proximal direction, and is illustrated in the remaining cross-sections J—J through F—F, where the angle (t) between the original line (2) and line (1) represents the twist angle for that cross-section. Preferably, the angle (t) of twisting throughout the mid-stem region ranges from about 0.50 degrees to about 8 degrees, most preferably from 3 degrees to 5 degrees. For example, in one preferred embodiment, the angle (t) in cross-section J—J is about 1 degree, in cross-section I—I, about 1.75 degrees, in cross-section H—H 2.75 degrees, in cross section G—G about 3.5 degrees, and in cross-section F—F about 4 degrees. The actual twisting ends at the proximal boundary, such that the angle (t) at cross-sections A—A through E—E (i.e. the proximal region) remains constant at 4 degrees, for example, relative the distal boundary.

III. Distal Region

The distal region (40) of the stem most preferably has a length ranging from about 1.2 to about 2 inches. Referring now to FIGS. 8–10, the inventive stem (10) comprises an internal slot (41) extending longitudinally through the distal end and along the distal (i.e. longitudinal) axis (Z) in order to reduce bending stiffness. Unlike some conventional "straight slot" designs, wherein bending is reduced only in the coronal plane, the present invention allows for a further reduction of bending stiffness in both the sagittal and coronal planes, thereby imparting more flexibility in the direction of the gait and stair climbing distal tip loads. Specifically, the inventive stem comprises a distal internal slot (41) that is rotated at an acute angle (b) to the coronal plane to cut the distal end into two separate tines, preferably a posterior/medial tine (44a) and an anterior/lateral tine (44b), as shown in FIGS. 8–10, for example. This angle (b) is defined by the intersection between an axis (42) that lies within the coronal plane and an axis (43) positioned centrally within the slot (41). Preferably, the angle of rotation (b) ranges from about 15 degrees to about 60 degrees, most preferably about 30 degrees. The length (L4) of the slot ranges from about 0.50 inch to about 2 inches, most preferably about 1 inch.

The distal region (40) further includes a distal end (40a) that is preferably elliptically tapered, as shown in FIGS. 8 and 11, for example. This distal end design functions to distribute the stress transferred to the femur over a larger area, and further decreases the magnitude of stress at any particular location. The elliptical configuration includes a semi-major diameter (d1) that is preferably about three times the length of the semi-minor diameter (d2).

The foregoing slot (41) is most preferably employed in stems having a distal diameter of greater than 11 mm (i.e. about 0.43 inches). Preferably, the width (W) of the slot is from about 0.09 inch to about 0.170 inch, most preferably about 0.125 inch.

The distal region may further include a groove (45) on the outer surface of one or more of the tines, most preferably both, to aid in reducing stiffness of the implant. As illustrated in FIG. 10, the groove (45) has a radius (R4) ranging from 0.1 to about 0.13 inches. The two radii (R5) of the remaining portion of each tine (44a, 44b) range in size of from about 0.10 inch to about 0.14 inch.

The foregoing disclosure and description of the invention are illustrative and explanatory thereof, and various changes in the size, shape, and materials, as well as in the details of the illustrated construction may be made without departing from the spirit of the invention.

We claim:

1. A prosthetic femoral hip stem comprising:
   (a) a longitudinal axis;
   (b) a distal region having a distal portion and a center, said longitudinal axis intersecting said center;

(c) a proximal region; and (d) a mid-stem region positioned between said distal and proximal regions;

wherein at least one cross-section taken perpendicular to said longitudinal axis through said proximal region includes:

(e) a substantially arcuate anterior side having a varying radius of curvature;

(f) a posterior side having a concavity;

(g) a substantially arcuate medial side having a radius of curvature;

(h) a substantially arcuate lateral side that slopes anteriorly to define an acute angle of declination; and (i) a substantially arcuate posterior/lateral corner having a radius of curvature larger than said medial side radius of curvature.

2. The stem of claim 1, wherein said angle of declination ranges from about 10 degrees to about 30 degrees.

3. The stem of claim 1, wherein said posterior concavity has a depth of from about 0.1 to about 3.0 mm.

4. The stem of claim 1, wherein said cross section further includes a substantially arcuate posterior/lateral corner having a radius of curvature larger than said medial side.

5. The stem of claim 1, wherein said cross section further includes a transition region connecting the posterior and medial sides, wherein said transition region has a radius of curvature larger than said medial side.

6. The stem of claim 1, wherein said stem further includes a twist about the distal axis.

7. The stem of claim 6, wherein said twist generally begins at a distal boundary of said mid-stem region and ends at a proximal boundary of said mid-stem region.

8. The stem of claim 7, wherein said twist in the mid-stem region is from about 0.50 degrees to about 8.0 degrees.

9. The stem of claim 1, wherein said distal region further includes an internal slot extending longitudinally through said distal end and along said distal axis.

10. The stem of claim 9, wherein a cross-section of said distal region taken perpendicular to said distal axis includes a first axis passing through said section in the medial/lateral direction and a second axis positioned centrally within said slot and perpendicular to said distal axis; wherein said first and second axes define an acute angle at said distal center to cut said distal region into two separate tines.

11. A prosthetic femoral hip stem comprising:

(a) a longitudinal axis;

(b) a proximal region;

(c) a distal region; and (d) a mid-stem region positioned between said distal and proximal regions;

wherein at least one cross-section taken perpendicular to said longitudinal axis through said proximal region includes:

(e) a substantially arcuate anterior side having a varying radius of curvature;

(f) a posterior side having a concavity;

(g) a substantially arcuate medial side having a radius of curvature;

(h) a substantially arcuate lateral side that slopes anteriorly to define an acute angle of declination;

(i) a substantially arcuate posterior/lateral corner having a radius of curvature larger than said medial side radius of curvature; and (j) an axis bisecting said cross section through said anterior and posterior sides an equidistance between said lateral and medial sides to define a first section including said lateral side and a second section including said medial side, said first section having a larger area than said second section.

12. The stem of claim 11, wherein said angle of declination ranges from about 10 degrees to about 30 degrees.

13. The stem of claim 11, wherein said posterior concavity has a depth of form about 0.1 mm to about 3.0 mm.

14. The stem of claim 11, wherein said cross section further includes a transition region connecting the posterior and medial sides, wherein said transition region had a radius of curvature larger than said medial side radius of curvature.

* * * * *

UNITED STATES PATENT AND TRADEMARK OFFICE
CERTIFICATE OF CORRECTION

PATENT NO. : 5,776,204
DATED : July 7, 1998
INVENTOR(S) : Philip C. Noble, Anthony K. Hedley, Michael J. Schulzki, and William J. Kelly, Jr.

It is certified that error appears in the above-indentified patent and that said Letters Patent is hereby corrected as shown below:

In column 6, line 29, after "curvature" insert -- (R3) --.

In column 6, line 43 and line 47, after "radius" insert -- of curvature --.

In column 7, line 5 and line 7, after "radius" insert -- of curvature --.

In claim 13, line 2, change "form" to -- from --.

Add substitute Fig. 1B, attached hereto.

In the drawings, Sheet 2 of 12 should be deleted to appear as per attatched.

Signed and Sealed this

Fifteenth Day of June, 1999

Q. TODD DICKINSON

Attest:

Attesting Officer

Acting Commissioner of Patents and Trademarks